US012667730B2

(12) United States Patent
Mangual-Soto

(10) Patent No.: US 12,667,730 B2
(45) Date of Patent: ***Jun. 30, 2026

(54) METHOD AND DEVICE FOR CONTROLLING CARDIAC RESYNCHRONIZATION THERAPY BASED ON HEART SOUNDS

(71) Applicant: Pacesetter, Inc., Sylmar, CA (US)

(72) Inventor: Jan O. Mangual-Soto, Rho (IT)

(73) Assignee: Pacesetter, Inc., Sylmar, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 18/490,576

(22) Filed: Oct. 19, 2023

(65) Prior Publication Data

US 2024/0042215 A1      Feb. 8, 2024

Related U.S. Application Data

(63) Continuation of application No. 17/353,172, filed on Jun. 21, 2021, now Pat. No. 11,826,575.

(60) Provisional application No. 63/076,976, filed on Sep. 11, 2020.

(51) Int. Cl.
*A61N 1/368* (2006.01)
*A61N 1/365* (2006.01)

(52) U.S. Cl.
CPC ..... *A61N 1/36843* (2017.08); *A61N 1/36578* (2013.01); *A61N 1/3682* (2013.01)

(58) Field of Classification Search
CPC ............ A61N 1/36843; A61N 1/36578; A61N 1/3682
See application file for complete search history.

(56) References Cited

U.S. PATENT DOCUMENTS

| | | | |
|---|---|---|---|
| 8,380,308 B2 | 2/2013 | Rosenberg et al. | |
| 10,391,316 B2 | 8/2019 | Zhang et al. | |
| 2012/0136406 A1 | 5/2012 | Min | |
| 2012/0157864 A1* | 6/2012 | Thakur | A61B 5/086 600/508 |
| 2013/0053913 A1* | 2/2013 | Koh | A61B 7/04 607/17 |
| 2014/0207013 A1* | 7/2014 | Lian | A61N 1/3712 600/523 |
| 2015/0202436 A1* | 7/2015 | Zielinski | A61N 1/36521 607/18 |

* cited by examiner

*Primary Examiner* — Brian T Gedeon
(74) *Attorney, Agent, or Firm* — Dean D. Small; Carroll, Hoette & Butscher, LLC

(57) ABSTRACT

A method for controlling an adaptive pacing therapy that includes utilizing one or more processors to perform measuring an atrial-ventricular (AV) interval corresponding to an interval between an atrial paced (Ap) event or an atrial sensed (As) event and a sensed ventricular (Vs) event, setting an AV delay based on the AV interval, and measuring an S1 heart sound characteristic of interest (COI) while utilizing the AV delay in connection with delivering a pacing therapy by the IMD. The one or more processors also perform adjusting the AV delay, repeating the measuring, and adjusting to obtain a collection of S1 heart sound COIs and corresponding AV delays, selecting one of the AV delays, that corresponds to a select one of the S1 heart sound COIs, as a resultant AV delay, and managing the pacing therapy, utilized by the IMD, based on the resultant AV delay.

20 Claims, 9 Drawing Sheets

METHOD AND DEVICE FOR CONTROLLING CARDIAC RESYNCHRONIZATION THERAPY BASED ON HEART SOUNDS

RELATED APPLICATION

The present application is a Continuation of U.S. Ser. No. 17/353,172, Titled "METHOD AND DEVICE FOR CONTROLLING CARDIAC RESYNCHRONIZATION THERAPY BASED ON HEART SOUNDS" which was filed on 21 Jun. 2021 that claimed priority to U.S. Provisional Application No. 63/076,976, Titled "METHOD AND DEVICE FOR CONTROLLING CARDIAC RESYNCHRONIZATION THERAPY BASED ON HEART SOUNDS" which was filed on 11 Sep. 2020, the complete subject matter of each which is expressly incorporated herein by reference in their entirety.

BACKGROUND

Embodiments of the present disclosure generally relate to methods and devices for controlling rate adaptive pacing.

Cardiac resynchronization therapy (CRT) has become the standard of care for patients with chronic heart failure (HF) and reduced ejection fraction (EF) that do not respond to pharmacological treatment. Adequate device programming is important to maintain consistent and effective therapy delivery. Inappropriate atrioventricular (AV) and ventricle-ventricle (VV) delay programming, or changes in intrinsic conduction timing, can lead to suboptimal therapy.

Previous studies have shown that there is a close relationship between heart sound and cardiac function. Yet heart sounds are not utilized to facilitate CRT.

SUMMARY

In accordance with embodiments herein, a method for controlling an adaptive pacing therapy using an implantable medical device (IMD) having electrodes proximate to an atrial (A) site and at least one ventricular site is provided. The method includes utilizing one or more processors to perform measuring an atrial-ventricular (AV) interval corresponding to an interval between an atrial paced (Ap) event or an atrial sensed (As) event and a sensed ventricular (Vs) event, setting an AV delay based on the AV interval, and measuring an S1 heart sound characteristic of interest (COI) while utilizing the AV delay in connection with delivering a pacing therapy by the IMD. The one or more processors also perform adjusting the AV delay, repeating the measuring, and adjusting to obtain a collection of S1 heart sound COIs and corresponding AV delays, selecting one of the AV delays, that corresponds to a select one of the S1 heart sound COIs, as a resultant AV delay, and managing the pacing therapy, utilized by the IMD, based on the resultant AV delay.

Optionally, the method also includes providing an electrode configured to be located proximate to an atrial (A) site, and providing an electrode configured to be located proximate to at least one of the following ventricular sites: left ventricular (LV) site, right ventricular (RV) site of the heart, or HIS site or left bundle branch (LBB) site of the heart. In one aspect, the pacing therapy is LV only pacing when the heart exhibits a left bundle branch block (LBBB). In another aspect, the pacing therapy is biventricular (BiV) pacing when the heart does not exhibit left bundle branch block (LBBB). In one example, the method also includes adjusting an AV delay based on the COI of the S1 heart sound and the AV interval. In another example, the method also includes setting a VV delay.

Optionally, the measuring the S1 heart sound COI also includes measuring the S1 heart sound COI while utilizing the VV delay in connection with delivering the pacing therapy by the IMD, and the method also includes adjusting the VV delay, and repeating the measuring and adjusting such that the collection of S1 heart sound COIs have corresponding AV delays and VV delays. The method also includes selecting one of the VV delays, that corresponds to a select one of the S1 heart sound COIs, as a resultant VV delay, and managing the pacing therapy, utilized by the IMD, based on the resultant VV delay. In one aspect, the measuring the S1 heart sound characteristic of interest (COI) comprises measuring the S1 heart sound COI with a three-dimensional accelerometer. Alternatively, the measuring the S1 heart sound COI with the three-dimensional accelerometer includes one of measuring the S1 heart sound COI on a single axis, or measuring the S1 heart sound COI based on a composite of at least two axes. In one example, setting the AV delay further comprises subtracting an AV offset from the AV interval. In another example, the method also includes obtaining a left bundle branch (LBB) block indicator indicative of whether a LBB block is present.

In one or more embodiments, a system for controlling an adaptive pacing therapy using an implantable medical device (IMD) having electrodes proximate to an atrial (A) site at least one ventricular site is provided. The system includes memory to store specific executable instructions, and one or more processors configured to execute the specific executable instructions. The specific executable instructions are for measuring an atrial-ventricular (AV) interval corresponding to an interval between an atrial paced (Ap) event or an atrial sensed (As) event and a sensed ventricular (Vs) event, setting an AV delay based on the AV interval, and measuring an S1 heart sound characteristic of interest (COI) while utilizing the AV delay in connection with delivering a pacing therapy by the IMD. The specific executable instructions are also for adjusting the AV delay, repeating the measuring, and adjusting to obtain a collection of S1 heart sound COIs and corresponding AV delays, selecting one of the AV delays, that corresponds to a select one of the S1 heart sound COIs, as a resultant AV delay, and managing the pacing therapy, utilized by the IMD, based on the resultant AV delay.

Optionally, the one or more processors also execute instructions for providing an electrode configured to be located proximate to an atrial (A) site, and providing an electrode configured to be located proximate to at least one of the following ventricular sites: left ventricular (LV) site of the heart, right ventricular (RV) site of the heart, or HIS site or left bundle branch (LBB) site of the heart. In one aspect, the pacing therapy is LV only pacing when the heart exhibits a left bundle branch block (LBBB). In another aspect, the pacing therapy is biventricular (BiV) pacing when the heart does not exhibit a left bundle branch block (LBBB). In one example, the one or more processors also are configured to execute instructions for adjusting an AV delay based on the COI of the S1 heart sound and the AV interval. In another example, the one or more processors are also configured to execute instructions for setting a VV delay.

Optionally, the measuring the S1 heart sound COI also includes measuring the S1 heart sound COI while utilizing the VV delay in connection with delivering the pacing therapy by the IMD, and the one or more processors are also configured to execute instructions for adjusting the VV delay, and repeating the measuring and adjusting such that the collection of S1 heart sound COIs have corresponding AV delays and VV delays. The one or more processors are also configured to execute instruction for selecting one of the VV delays, that corresponds to a select one of the S1 heart sound COIs, as a resultant VV delay, and managing the pacing therapy, utilized by the IMD, based on the resultant VV delay. In one aspect, the system also includes a three-dimensional accelerometer coupled to the one or more processors to measure the S1 heart sound characteristic of interest (COI). In another aspect, the three-dimensional accelerometer measures one of the S1 heart sound COI on a single axis, or the S1 heart sound COI based on a composite of at least two axes. In one example, setting the AV delay further comprises subtracting an AV offset from the AV interval. In another example, the one or more processors are also configured to execute instructions for obtaining a left bundle branch (LBB) block indicator indicative of whether an LBB block is present.

DETAILED DESCRIPTION

Figure 1:
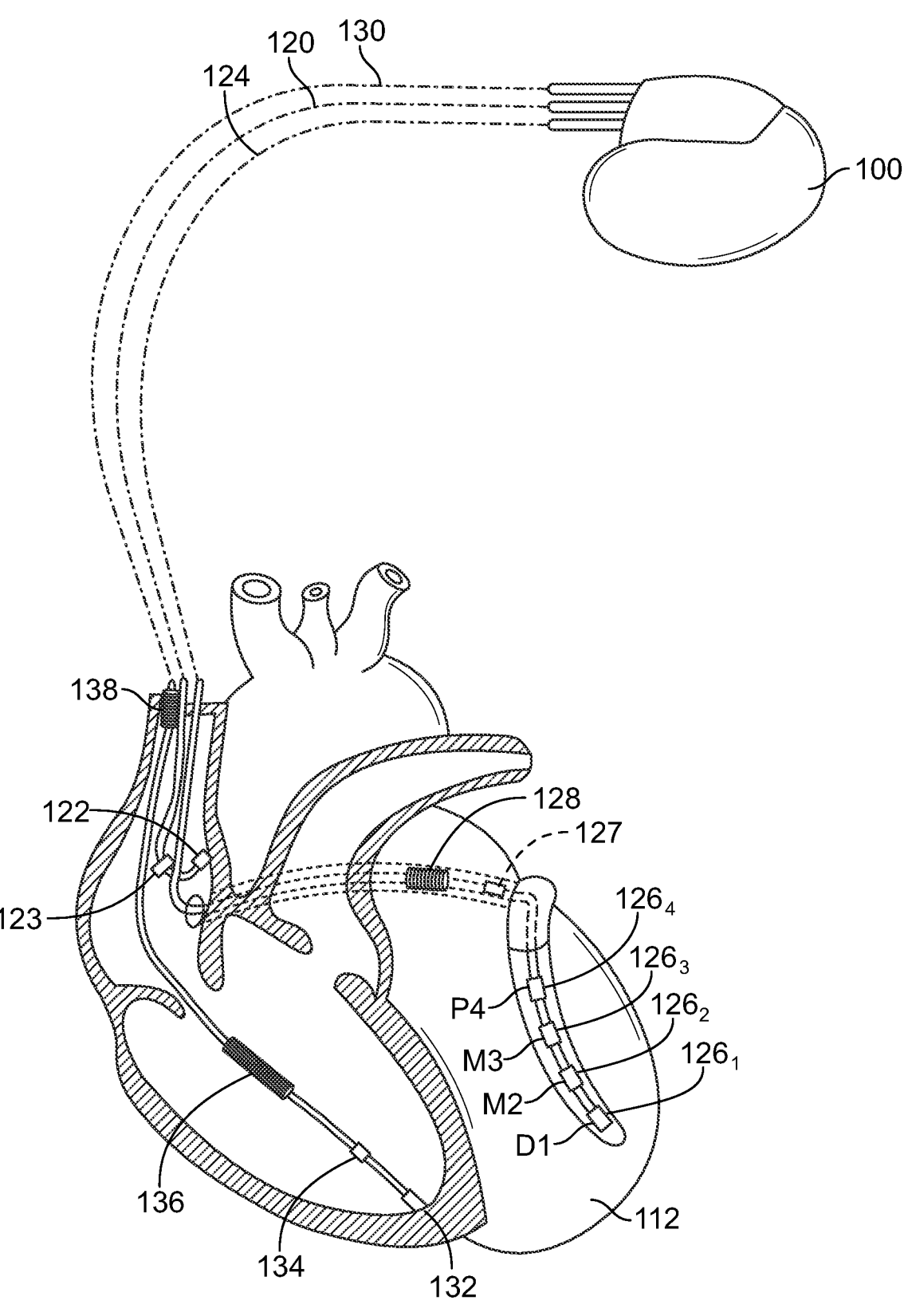
FIG. 1 illustrates an exemplary IMD formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The terms "atrial-ventricular delay", "AV delay" and "AVD" refer to a programmed time delay to be used by the implantable medical device in connection with delivering therapy. In one example the AV delay is a pacing parameter that is set as a time delay between an occurrence of an intrinsic or paced event in an atria and a time at which the IMD will deliver a pacing pulse in a right ventricle (RV) or a left ventricle (LV), unless an intrinsic ventricular event occurs earlier. In an example embodiment, adjusting the AV delay can include setting the programmed time delay based on a heart sound of interest (S1, S2, S3, S4).

The terms "ventricular-ventricular delay", "VV delay" and "VVD" refer to a programmed time delay to be used by the implantable medical device in connection with delivering therapy. In one example the VVD is a pacing parameter that is set as a time delay between an occurrence of an intrinsic or paced event in a ventricle and a time at which the IMD will deliver a pacing pulse in the other ventricle.

The term "LV only pacing" refers to a mode of operation for an implanted medical device in which the LV is paced but the RV is not paced.

The term "heart sound characteristic of interest", or "heart sound COI" as used herein refers to any signal, measurement, parameter, etc. related to a heart sound. In one example, a heart sound COI is a signal detected by an accelerometer that is proportional to a heart sound. In another example, a heart sound COI is a signal detected by a diaphragm that detects acoustic waves. In yet another example, a heart sound COI includes a signal obtained by a leadless medical device and related to an electrocardiogram. In another example, the heart sound COI is a signal obtained from a haptic sensor that senses vibration corresponding to the heart sounds. In yet another example, the heart sound COI is a signal obtained from a subcutaneous IMD (S-IMD) that includes a pulse generator, and obtains signals related to heart sounds. To this end, the signal, measurement, parameter, etc. may be based on a vibration, movement, sound wave, or the like. The heart sound COI may also be detected by other measurement or sensing devices.

Embodiments may be implemented in connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

A system is provided for controlling an adaptive pacing therapy using an implantable medical device (IMD) having electrodes proximate to an atrial (A) site at least one ventricular site. An S1 heart sound is used to determine adjustments in pacing. In particular, if a patient has a measured PR interval that is less than a threshold duration, such as 250 ms, and a left bundle branch block (LBBB) (identified by A-RVs shorter than A-LVs, or user identified) LV only pacing from the latest activating electrode ($LV_{late}$) is provided. Offsets are then programmed, and S1 sound delays are recorded such that the offset corresponding to the narrowest S1 sound signal may be used to adjust pacing. If LBBB is not present and/or the PR interval is greater than the threshold duration, biventricular pacing is provided (RV+LV simultaneous pacing). During biventricular pacing, S1 sound delays are measured at varying programmed AV delay (i.e. 140 ms up to 200 ms, with 20 ms increments). S1 sound delays are then recorded and the AV delay resulting in the narrowest S1 sound signal is used to guide pacing.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the CS region via the CS OS for positioning a distal electrode adjacent to the left ventricle and/or additional electrode(s) adjacent to the left atrium. An exemplary LV lead 124 is designed to receive atrial and ventricular cardiac signals and to deliver left ventricular pacing therapy using a set of four left ventricular electrodes 126₁, 126₂, 126₃, and 126₄ (thereby providing a quadripole lead), left atrial pacing therapy using at least a left atrial ring electrode 127, and shocking therapy using at least a left atrial coil electrode 128 implanted on or near the left atrium.

In accordance with embodiments herein, methods and devices are provided that utilize S1 heart sounds to determine therapeutic pacing of the IMD. Specifically, the methods and devices measure a first heart sound S1, such as utilizing a three-dimensional accelerometer in the IMD. In particular, the methods and devices are further configured to switch from the BiV pacing therapy to a left univentricular (LV only) pacing therapy that delivers pacing stimulation at one or more left ventricular sites and does not deliver any pacing stimulation to any right ventricular sites. Once the pacing therapy is determined, the system may determine the effects of different offsets during pacing on the S1 sound to determine the offset for pacing.

While illustrated as an implantable cardiac monitor (ICM), in other example embodiments the IMD can be a leadless device. Optionally, the leadless device can include a housing, multiple electrodes coupled to the housing, and a pulse generator hermetically contained within the housing and electrically coupled to the electrodes. A pulse generator may be provided and configured for sourcing energy internal to the housing, generating, and delivering electrical pulses to the electrodes. A controller can also be hermetically contained within the housing as part of the pulse generator and communicatively coupled to the electrodes. The controller can control, among other things, recording of physiologic characteristics of interest and/or electrical pulse delivery based on the sensed activity.

Optionally, a first leadless device can be located in the right atrium (RA), while a second leadless device is located in the right ventricle (RV). The leadless devices coordinate the operation therebetween based in part on information conveyed between the leadless devices during operation. The information conveyed between the leadless devices may include, among other things, physiologic data regarding activity occurring in the corresponding local chamber. For example, the atrial leadless device may perform sensing, including for heart sounds S1, S2, S3, or S4, and pacing operations in the right atrium, while the ventricular leadless device may perform sensing, including heart sound sensing, and pacing operations in the right ventricle.

Alternatively, leadless devices can be located in the RV or left ventricle (LV) to obtain physiologic data regarding atrial activity, including heart sounds S1, S2, S3, or S4. In addition, optionally, the leadless device could be located in the RV or LV to obtain physiologic data regarding activity in one of the LV or RV in order to determine and set a VV delay.

Alternatively, the leadless devices may be located in other chamber combinations of the heart, as well as outside of the heart. Optionally, the leadless devices may be located in a blood pool without directly engaging local tissue. Optionally, the leadless devices may be implemented solely to perform monitoring operations, without delivery of therapy. As another example, one or more leadless devices may represent a subcutaneous implantable device located in a subcutaneous pocket and configured to perform monitoring and/or deliver therapy.

Optionally, the leadless devices include electrodes that are located directly on the housing of the device, without a lead extending from the device housing. Alternatively, the leadless device may be implemented with leads, where the conducted communication occurs between one or more electrodes on the lead and/or on the housing. Examples of other IMDs that may be configured to implement the conducted communication embodiments described herein are described in U.S. Pat. No. 9,168,383, issued Oct. 27, 2015, and titled "LEADLESS CARDIAC PACEMAKER WITH CONDUCTED COMMUNICATION," the complete subject matter of which is incorporated by reference in its entirety.

In particular embodiments, the IMD can be a subcutaneous IMD (S-IMD) that includes a pulse generator that is positioned within a pectoral region of a chest of a patient. Embodiments can also include a lead having first and second electrode segments with the first electrode segment positioned along an anterior of the chest of the patient and the second electrode segment positioned along a posterior of the patient. The first and second electrode segment may obtain physiologic data regarding cardiac activity, including heart sounds S1, S2, S3, or S4.

Implantable Medical Device and Accelerometer

Figure 2:
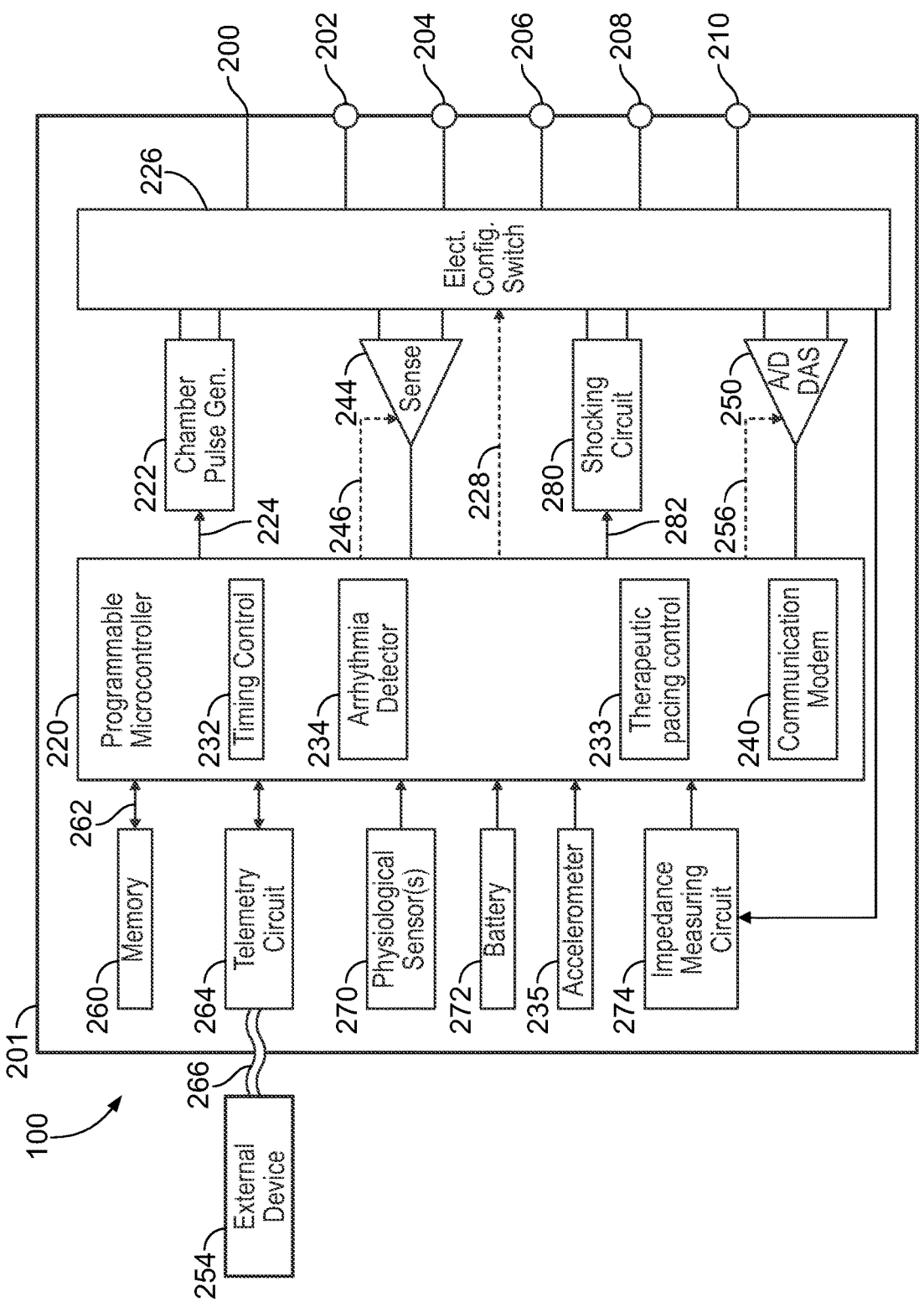
FIG. 2 shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing, and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing. As described herein, the IMD 100 is configured to provide LUV pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

Microcontroller 220 is illustrated to include timing control circuitry 232 to control the timing of the stimulation pulses (e.g., pacing rate, atrioventricular (AV) delay, atrial interconduction (A-A) delay, or ventricular interconduction (V-V) delay, etc.). In connection with embodiments herein, the timing control circuitry 232 is used to manage an AV delay or VV delay that is set as described herein to support pacing therapy. Microcontroller 220 also has an arrhythmia detector 234 for detecting arrhythmia conditions and a morphology detector to review and analyze one or more features of the morphology of cardiac signals.

The microcontroller 220 includes therapeutic pacing control circuitry 233 that is utilized with an accelerometer 235 to implement the processes described herein for controlling a pacing therapy. The control circuitry 233 is configured to measure an atrial-ventricular (AV) interval corresponding to an interval between an atrial paced (Ap) event or an atrial sensed (As) event and a sensed ventricular (Vs) event, and set an AV delay based on the AV interval. The control circuitry 233 based on signals received from the accelerometer 235 also measures an S1 heart sound characteristic of interest (COI) while utilizing the AV delay in connection with delivering a pacing therapy by the IMD and adjusts the AV delay. The S1 heart sound COI in one example is received from the accelerometer 235. The accelerometer 235 can sense a heart sound COI from any heart sound including S1, S2, S3, or S4. The heart sound COI can be based on a combination of heart sounds, including the interval between S1 and S2, between S2 and S3, between S3 and S4, any other combination or permutation, or the like. In yet another example, the heart sound COI can be a duration of any one heart sound, combination of heart sounds, etc.

In one example, the accelerometer can be implemented utilizing all or portions of the structural and/or functional aspects of the methods and systems described in U.S. Pat. No. 6,937,900, titled "AC/DC Multi-Axis Accelerometer for Determining A Patient Activity and Body Position;" U.S. application Ser. No. 17/192,961, filed Mar. 5, 2021, titled "SYSTEM FOR VERIFYING A PATHOLOGIC EPISODE USING AN ACCELEROMETER"; U.S. application Ser. No. 16/869,733, filed May 8, 2020, titled "METHOD AND DEVICE FOR DETECTING RESPIRATION ANOMALY FROM LOW FREQUENCY COMPONENT OF ELECTRICAL CARDIAC ACTIVITY SIGNALS;" U.S. application Ser. No. 17/194,354, filed Mar. 8, 2021, titled "METHOD AND SYSTEMS FOR HEART CONDITION DETECTION USING AN ACCELEROMETER," the complete subject matter which is expressly incorporated herein by reference.

The control circuitry 233 repeats the measuring and adjusting to obtain a collection of S1 heart sound COIs and corresponding AV delays, and selects one of the AV delays, that corresponds to a select one of the S1 heart sound COIs, as a resultant AV delay. In one example adjusting the AV delay includes setting a timer based on a heart sound of interest (S1, S2, S3, S4). The timer can be an AV delay, VV delay, a refractory period, blanking period, etc. The control circuitry 233 also manages a pacing therapy, utilized by the IMD, based on the resultant AV delay.

The control circuitry 233 is configured to then deliver a pacing therapy based on the AV delay. For example, the control circuitry 233 may be configured to deliver a biventricular (BiV) pacing therapy. The control circuitry 233 is configured to switch from the BiV pacing therapy to a left univentricular pacing (LV pacing only) therapy that delivers pacing stimulation at one or more left ventricular sites and does not deliver any pacing stimulation to any right ventricular sites when LBBB is present.

The IMD 100 is further equipped with a communication modem (modulator/demodulator) 240 to enable wireless communication with other devices, implanted devices, and/ or external devices. The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuit 244 selectively coupled to one or more electrodes that perform sensing operations, through the switch 226 to detect the presence of cardiac activity in the right chambers of the heart. The sensing circuit 244 may include dedicated sense amplifiers, multiplexed amplifiers, or shared amplifiers. The output of the sensing circuit 244 is connected to the microcontroller 220 which, in turn, triggers or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit.

The IMD 100 further includes an analog-to-digital (A/D) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The memory 260 may be configured to include patient data, including whether a patient has LBBB. In particular, the control circuitry can determine if a patient has LBBB or can obtain the patient data from the memory.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity. Signals generated by the physiological sensors 270 are passed to the microcontroller 220 for analysis. The microcontroller 220 responds by adjusting the various pacing parameters (such as rate, AV Delay, VV Delay, etc.) at which the atrial and ventricular pacing pulses are administered.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The IMD 100 further includes an impedance measuring circuit 274 that is enabled by the microcontroller 220 via a control signal 282.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282.

Figure 3:
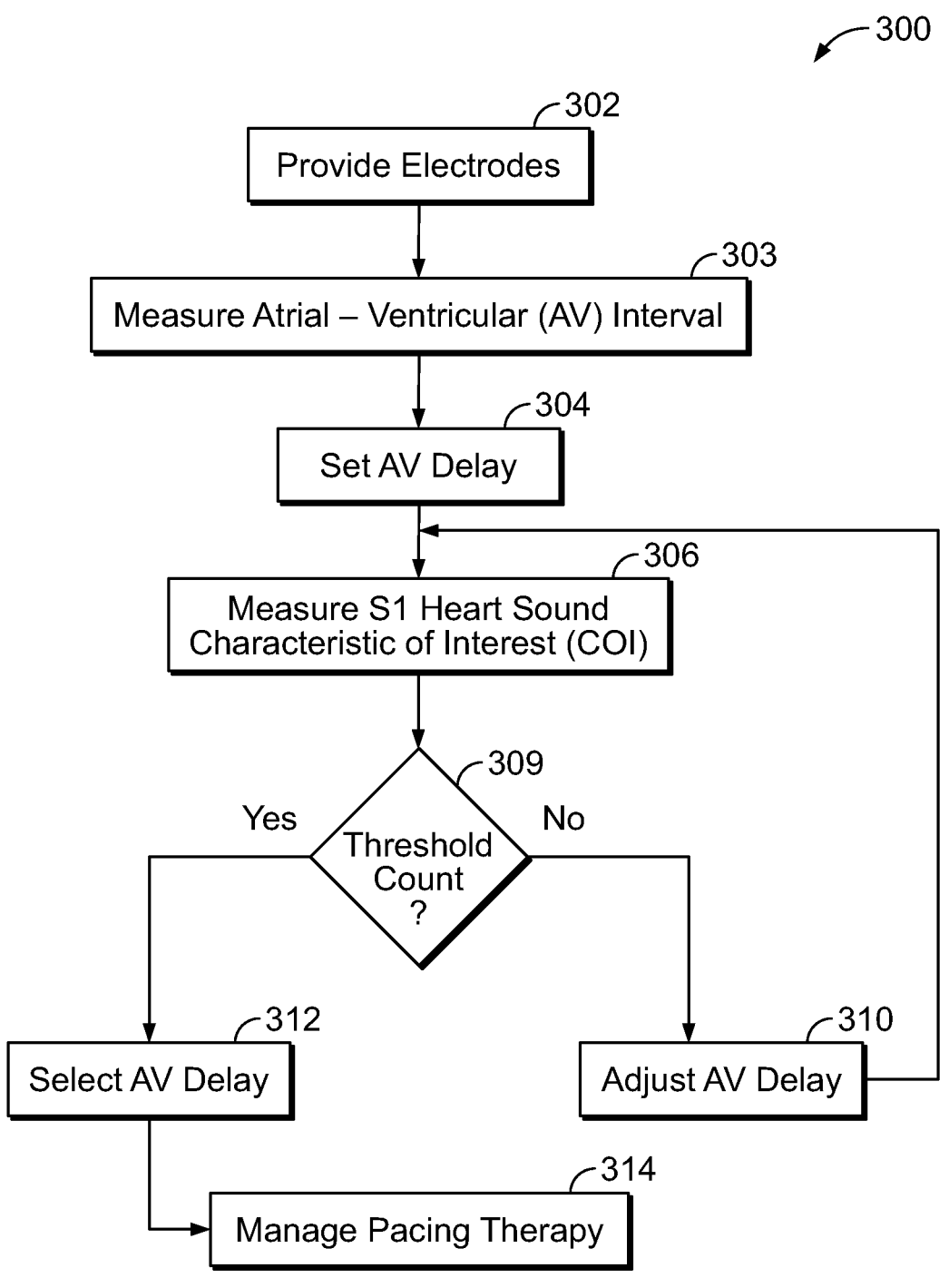
FIG. 3 illustrates a process for controlling an adaptive pacing therapy in accordance with embodiments herein.

FIG. 3 illustrates a process 300 for controlling an adaptive pacing therapy using an implantable medical device (IMD) having electrodes proximate to an atrial (A) site and at least one ventricular site. All or a portion of the operations of FIG. 3 may be performed by one or more processors of an IMD, an external device, a server operating on a medical network and the like. The operations of FIG. 3 may be implemented in combination with the systems and methods described in U.S. Pat. No. 7,778,706, titled "Rate Adaptive Biventricular and Cardiac Resynchronization Therapy" (the '706 patent) and/or U.S. Pat. No. 7,702,390, titled "Rate Adaptive Biventricular and Cardiac Resynchronization Therapy" (the '390 patent), the complete subject matter both of which are incorporated herein by reference.

At 302, the one or more processors provide one or more electrodes configured to be located proximate to an atrial (A) site and one or more electrodes configured to be located proximate to at least one of the following ventricular sites: left ventricular (LV) site, right ventricular (RV) site of the heart, HIS site or left bundle branch (LBB) site of the heart. In one example, the electrodes are the electrodes as described in relation to FIGS. 1-2.

At 303, the one or more processors measure an atrial-ventricular (AV) interval corresponding to an interval between an atrial paced (Ap) event or an atrial sensed (As) event and a sensed ventricular (Vs) event. The interval may correspond to a time interval between peaks or another characteristic of interest from the Ap/As event and Vs event. At 304, the one or more processors set an AV delay based on the AV interval. In one example, the AV delay is set by determining an AV offset, and subtracting the AV offset from the AV interval. For example, the AV offset may be a predetermined amount of time stored in memory, a percentage of the AV interval, or the like. The AV offset may be determined by aggregating patient data or determining an AV offset that has been successful for previous patients.

At 306, the one or more processors measure an S1 heart sound and determine an S1 characteristic of interest (COI) while utilizing the AV delay in connection with delivering a pacing therapy. In one example, the COI of the S1 heart sound is the duration of the S1 heart sound. To this end, the COI can be a range of S1 heart sound durations (e.g., 80 ms-120 ms) that represent a range when associated with the duration of a healthy heart. The duration of the S1 heart sound extends between a first deflection of the S1 heart sound and an ending point for the last deflection of the S1 heart sound. Alternatively, the COI may be a narrowest or shortest duration from a collection of the S1 heart sounds. The S1 heart sound COI may be measured by a three-dimensional accelerometer using any of the techniques as described herein in relation to FIG. 8 and/or in one or more of the patents and applications referenced herein. For example, an accelerometer may be used to provide either two dimensional or three dimensional information regarding an S1 heart sound. Specifically, the accelerometer may receive S1 heart sound data from a single axis, or alternatively can receives composite S1 heart sound data separately along three individual axes.

In one embodiment, the patient is placed at a predetermined position, such as a supine position, and measurements are taken to collect S1 hears sound data components along all three axes (X-axis, Y-axis, and Z-axis). Based on the measurements, the Y-axis may provide the best reading of the S1 heart sound. As such, when taking future reading in a supine position, the Y-axis heart sound data component may be selected as the sole or primary source of S1 hears sound data. Alternatively, the S1 heart sound data may be collected while the patient is in a sitting position where a composite reading of the three axes provides the best S1 heart sound data. In this manner, during future monitoring and testing, when the patient is sitting, a composite reading along to or more axis of the S1 heart sound data is utilized.

Figure 4:
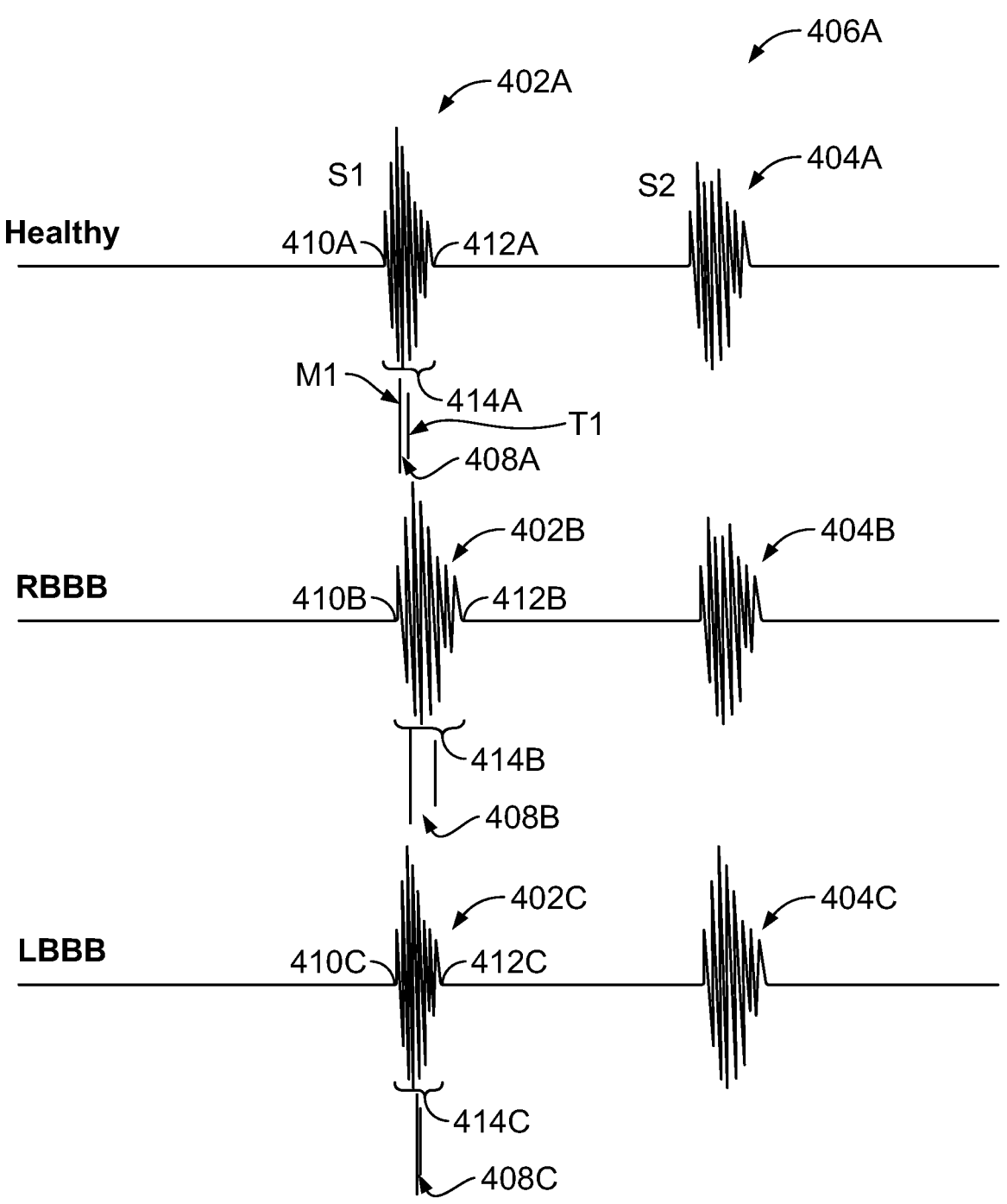
FIG. 4 illustrates graphs of heart sounds, in accordance with embodiments herein.

FIG. 4 represents a comparison of S1 heart sounds 402A-C and S2 heart sounds 404A-C measured over time. In particular, in healthy adults, the most common heart sounds are S1 and S2, corresponding to the closing of the atrioventricular valves and semilunar valves, respectively. S1 is caused by the closing of the mitral (M1) and tricuspid (T1) valves, at the beginning of ventricular contraction (systole). In a normal heart, S1 is 'split' due to M1 preceding T1, with a more pronounced separation in patients with RBBB. In contrast, LBBB causes M1 and T1 to merge, leading to an absent split of the S1 signal.

The upper panel of heart sounds at 406A illustrates the S1 heart sound 402A and S2 heart sound 404A of a healthy heart. In particular, the M1 to T1 interval 408A is illustrated for the S1 heart sound 402A. The middle panel of heart sounds at 406B illustrates the S1 heart sound 402B and S2 heart sound 404B for a heart experiencing RBBB. As illustrated, the M1 to T1 interval 408B for the heart experiencing RBBB is greater than the M1 to T1 interval 408A for the healthy heart. Similarly, the bottom panel of heart sounds at 406C illustrates the S1 heart sound 402C and S2 heart sound 404C for a heart experiencing LBBB. As illustrated, the M1 to T1 interval 408C for the heart experiencing LBBB is less than the M1 to T1 interval 408A for the healthy heart. To this end, when the M1 to T1 interval 408A-C decreases in size, it becomes more likely that the heart will experience LBBB. In addition, by decreasing the M1 to T1 interval, the S1 sound duration 414A-414C from the beginning of the S1 heart sounds 410A-410C to the termination/end of the S1 detected heart sounds 412A-412C is similarly decreased. In this manner, the duration 414A-414C of S1 between the beginning 410A-410C and end 412A-412C is proportional to the size of the M1 to T1 interval 408A-408C. In one example, a three-dimensional accelerometer is used to measure the S1 sound duration 414A-414C.

By monitoring the S1 heart sound 402A-C, and in particular, the S1 sound duration 414A-C, determinations may be made regarding whether a heart is healthy, experiencing LBBB or RBBB. To this end, by adjusting pacing based on the S1 sound duration 414A-C, the S1 sound duration 414A of a healthy heart can be achieved, even when LBBB or RBBB is present. As a result, improved CRT is provided. As such an S1 sound interval, or duration range may be defined, wherein S1 sound durations that are below a lower threshold or range are indicative of LBBB. Similarly, when an S1 sound interval/duration exceeds an upper threshold or range, the process may determine that the patient is experiencing RBBB. Consequently, the pacing may be adjusted to maintain the S1 sound duration between the lower and upper thresholds during pacing therapy.

Returning to FIG. 3, at 309, the one or more processors determine if a count threshold has been met regarding the number of measurements taken. For example, it may be desirable to collect S1 heart sound measurements in connection with a predetermined number of different AV delays. In one example, S1 heart sound measurements are collected in connection with five different AV delays, while in the examples less than five or more than five measurements are taken. If the threshold is not exceeded at 309, then flow moves to 310.

At 310, the one or more processors adjust the AV delay based on the S1 heart sound COI. For example, the AV delay may be increased or decreased by a predetermined amount based on whether the S1 heart sound COI is above or below a threshold. As a further example, the AV delay may be increased or decreased by an amount that has a relation (e.g., is proportional) to an amount that the S1 heart sound COI is above or below the corresponding threshold. Thereafter, flow returns to 306 where additional measurements are collected and analyzed to obtain additional COI.

At 312, the one or more processors analyze the COI for the collection of S1 heart sounds. The one or more processors identify a preferred one of the AV delays, that corresponds to a select one of the S1 heart sound COIs, as a resultant AV delay. COIs may include S1 heart sound duration, S1 heart sound M1 to T1 duration, or the like. For example, a first AV delay of 140 ms may result in a S1 heart sound duration of 30 ms, a second AV delay of 160 ms may result in a S1 heart sound duration of 40 ms, and a third AV delay of 180 ms may result in a S1 heart sound duration of 50 ms. In such an example, the one or more processors may select the AV delay of 140 ms associated with the shortest S1 heart sound duration of 30 ms. Alternatively, when the COI of the S1 heart sound duration is 30 ms, the process, or user programmed interval, may consider this duration too short, and thus select the second AV delay of 160 ms. The one or more processors may make the selection based on a look-up table, decision tree, algorithm, mathematical function, etc.

At 314, the one or more processors manage a pacing therapy, utilized by the IMD, based on the resultant AV delay. In one example, the pacing therapy is LV only pacing when the heart exhibits LBBB. Alternatively, the pacing therapy is biventricular (BiV) pacing when the heart does not exhibit LBBB.

Figure 5:
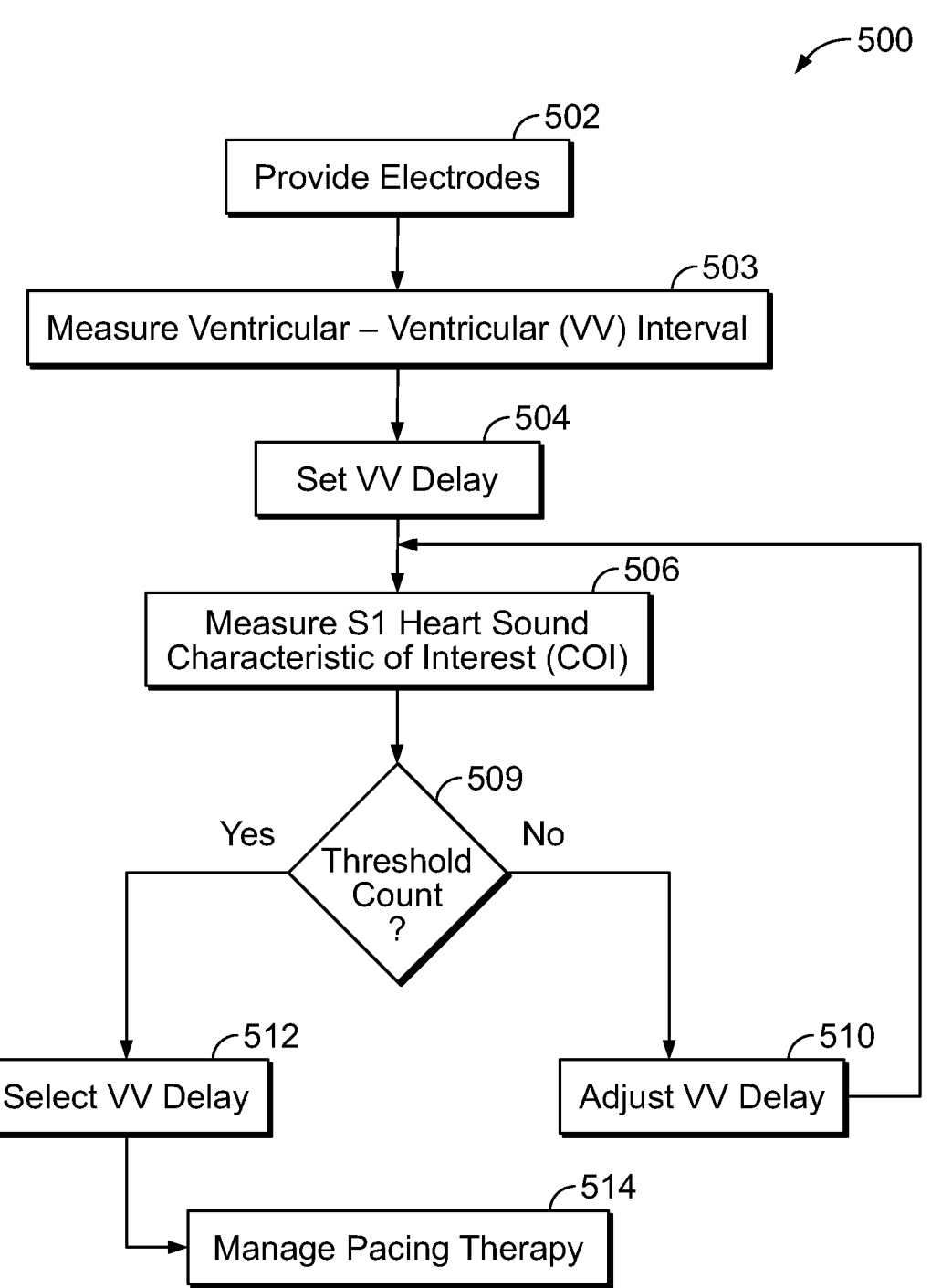
FIG. 5 illustrates a process for controlling an adaptive pacing therapy in accordance with embodiments herein.

FIG. 5 illustrates a process 500 for controlling an adaptive pacing therapy using an implantable medical device (IMD) having electrodes proximate to an atrial (A) site and at least one ventricular site. In this embodiment, a VV delay is set by the IMD, and pacing therapy is managed based on the VV delay. In one example, the VV delay-based process is utilized in addition to the AV delay-based process as described in relation to FIG. 3. Alternatively, the VV delay-based process is utilized instead of the AV delay-based process described in relation to FIG. 3. Similar to the process 300, all, or a portion of the operations of FIG. 5 may be performed by one or more processors of an IMD, an external device, a server operating on a medical network and the like. The operations of FIG. 5 may be implemented in combination with the systems and methods described in U.S. Pat. No. 7,778,706, titled "Rate Adaptive Biventricular and Cardiac Resynchronization Therapy" (the '706 patent) and/or U.S. Pat. No. 7,702,390, titled "Rate Adaptive Biventricular and Cardiac Resynchronization Therapy" (the '390 patent), the complete subject matter both of which are incorporated herein by reference.

At 502, the one or more processors set a VV delay. The VV delay may be preprogrammed by a clinician at the time of implant and/or subsequently during a clinical visit, or alternatively automatically based on various measurements and analysis performed by the IMD. At 504, the one or more processors adjust the VV delay. In one example, the VV delay is set by determining a VV offset and subtracting the VV offset from the VV interval. For example, the VV offset may be a predetermined amount of time stored in memory, a percentage of the VV interval, or the like. The VV offset may be determined by aggregating patient data or determining a VV offset that has been successful for previous patients.

At 506, the one or more processors measure an S1 heart sound and determine an S1 characteristic of interest (COI) while utilizing the VV delay in connection with delivering a pacing therapy. The S1 heart sound is measured utilizing any process or method described herein as well as the processes described in the patents and patent applications referenced herein. The measurements may be collected while a patient is oriented in one or more predetermined orientations.

At 509 the one or more processors determine if a count threshold has been met regarding the number of measurements taken. For example, it may be desirable to collect S1 heart sound measurements in connection with a predetermined number of different VV delays. In one example, S1 heart sound measurements are collected in connection with five different VV delays, while in the examples less than five or more than five measurements are taken. If the threshold is not exceeded at 509, then flow moves to 510.

At 510, the one or more processors adjust the VV delay based on the S1 heart sound COI. For example, the VV delay may be increased or decreased by a predetermined amount based on whether the S1 heart sound COI is above or below a threshold. As a further example, the VV delay may be increased or decreased by an amount that has a relation (e.g., is proportional) to an amount that the S1 heart sound COI is above or below the corresponding threshold. Thereafter, flow returns to 506 where additional measurements are collected and analyzed to obtain additional COI.

At 512, the one or more processors analyze the COI for the collection of S1 heart sounds. The one or more processors identify a preferred one of the VV delays, that corresponds to a select one of the S1 heart sound COIs, as a resultant VV delay.

Figure 6:
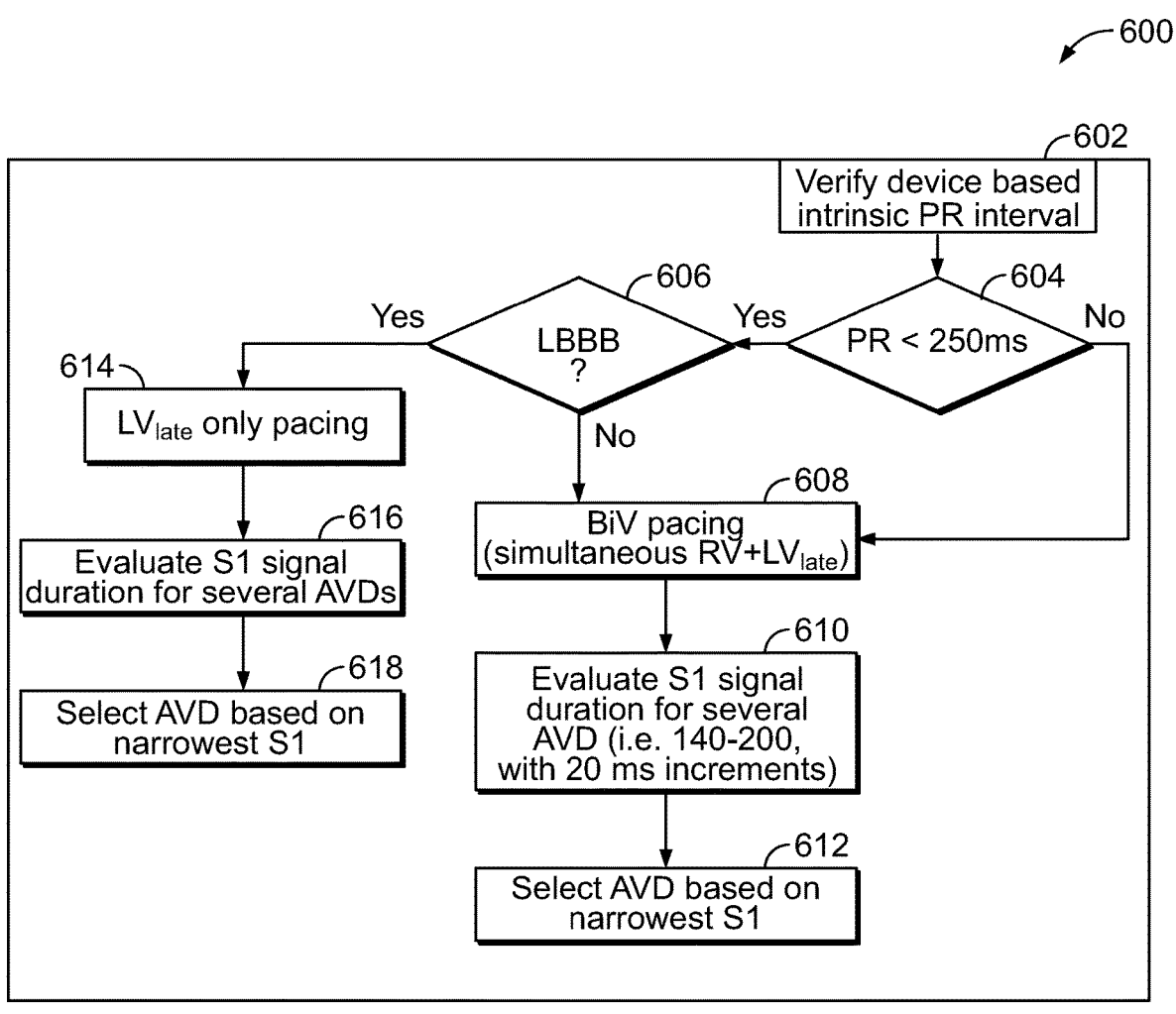
FIG. 6 illustrates a process for selecting a therapy treatment in accordance with embodiments herein.

FIG. 6 is a process 600 for selecting a therapy treatment based on heart sounds. At 602, the one or more processors monitor cardiac activity signals to determine a CA COI. An ECG or IEGM or the like can be utilized to determine the heart parameter. In one example, the COI is the interval between intrinsic atrial and ventricular events (e.g., the PR interval). The PR interval may be used to indicate that a patient may have LBBB. In one example, the PR interval may be a threshold interval used to identify a candidate LBBB. In addition, the one or more processors analyze CA signals detected at multiple LV sensing sites and determine the one of the LV sensing sites that experience the intrinsic activation at a predetermined time relative to the other LV sensing sites. For example, the one or more processors may determine the last LV sensing site to experience the intrinsic activation, thereafter designated as the $LV_{late}$ sensing site.

Figure 7:
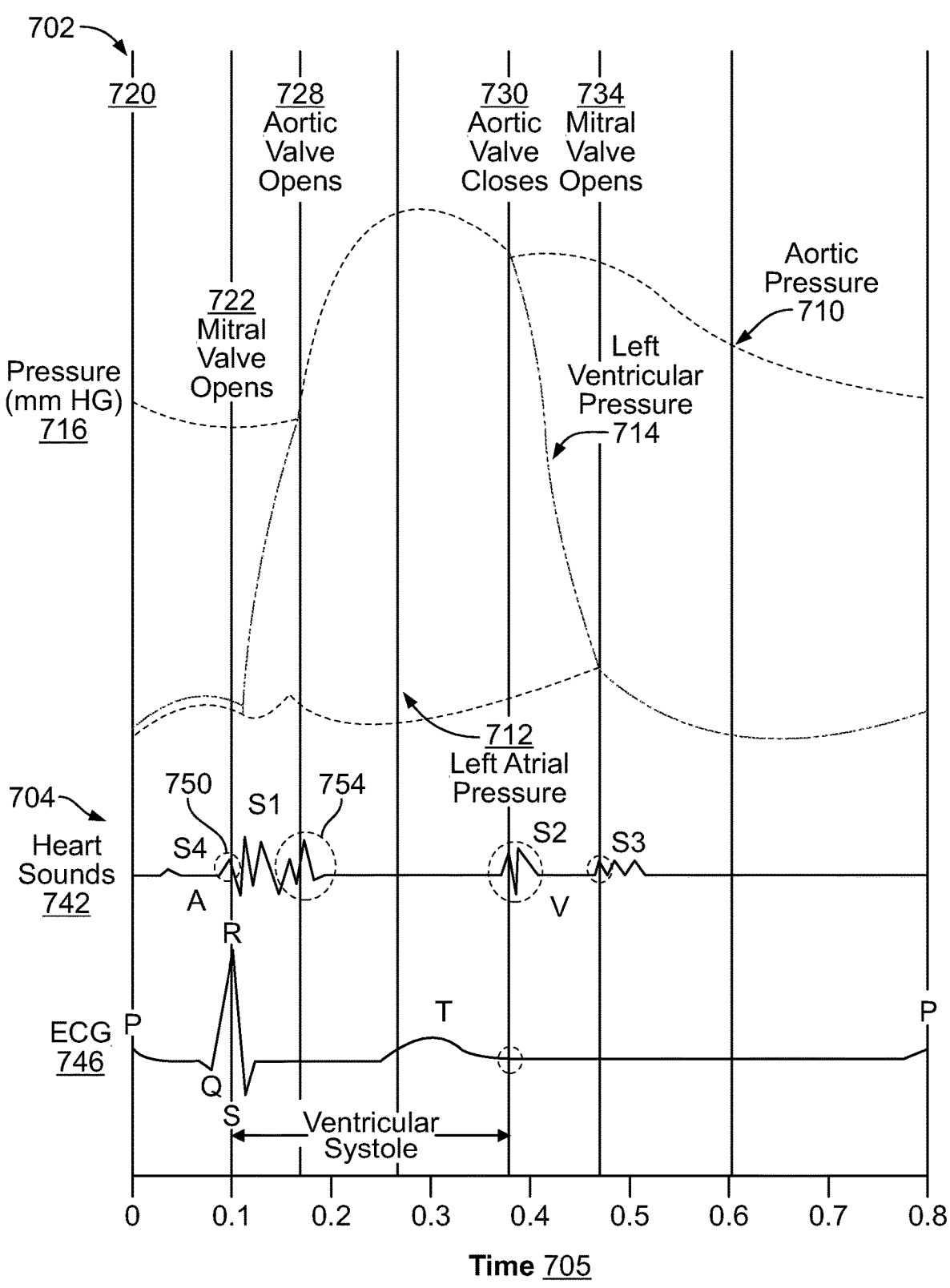
FIG. 7 illustrates an example anatomical diagram of certain parameters measured over a cardiac cycle.

FIG. 7 illustrates an example anatomical diagram of certain parameters measured over a cardiac cycle. Plot 702 represents blood pressure parameters, while plot 704 represents examples of heart sound and ECG parameters indicative of cardiac valve events. Both plots are illustrated in relation to time 705 along the horizontal or x-axis where the duration of time 705 represents one cardiac cycle lasting approximately 0.8 seconds. Plot 702 presents aortic pressure as dotted line 710, left atrial pressure as dashed line 712, and left ventricular pressure as line 714 (alternating dashes and dots). Pressure values for the aortic, left atrial, and left ventricle pressures are represented vertically along the y-axis as pressure in millimeter of mercury (mm HG) 716. For purposes of explanation, starting arbitrarily at the leftmost portion 720 of plot 702 assume that the patient's mitral valve is open, and the aortic valve is closed. At this point in the cardiac cycle, the left atrium is contracting, and the left ventricle is relaxed. During these conditions, blood is flowing freely from the left atrium into the left ventricle. Subsequently, the left ventricle begins to contract, and at about the same time, the mitral valve closes as indicated at 722. When looking specifically at left atrial pressure 712, hemodynamics indicates that for a period between point 720 and mitral valve closing 722 that blood pressures within the left atrium and the left ventricle are approximately equal.

Continuing with plot 702, at point 728 the aortic valve leading from the left ventricle into the aorta opens. With the opening of the aortic valve, blood flows from the left ventricle into the aorta and pressures within the left ventricle and the aorta generally equalize. Pressure within the left ventricle and the aorta remain generally equal until the aortic valve closes at point 730. The closing of the aortic valve at 730 causes the left ventricle to be fluidly separated from the aorta. Subsequently, as the left ventricle relaxes its volume expands resulting in decreasing pressures within the left ventricle until the mitral valve opens at 734.

Plot 704 provides examples for detecting cardiac valve events related to the mitral and aortic valves. Parameter 742 relates to heart sound data and parameter 746 relates to electrocardiogram (ECG) data. Heart sound parameter 742 includes 4 distinct heart sounds indicated as S1, S2, S3, and S4. Heart sounds can be detected with various types of detection mechanisms. For instance, heart sounds can be sampled with accelerometers, microphones, and or pressure transducers, among others. The heart sound detection mechanisms can be positioned external to a patient or internally. The heart sound detection mechanism may be positioned internally the patient, such as within the housing of an IMD. Additionally or alternatively, the heart sound detection mechanism can be positioned upon a lead that is positioned in the patient's vasculature or heart. The mitral valve closure corresponds to the S1 heart sound generally. Specifically, a first positive peak 750 of the S1 heart sound generally corresponds to mitral valve closure as evidenced along the vertical axis. Aortic valve opening 728 can be detected from the heart sound parameter 742 as a last peak 754 of heart sound S1.

Electrogram parameter 746 includes peaks or waves labeled as "P", "Q", "R", "S", and "T". Electrogram data can be detected with various mechanisms. Other mechanisms can sense electrogram data externally via one or more sensors positioned upon the patient's skin proximate the thorax.

In the example of FIG. 7, the heart behaves in a relatively normal physiologic manner and the heart sound S1 occurs after a peak of the QRS complex (and after the evoked response at the proximal LV site). However, patients with LBBB will experience certain abnormalities in the conduction pattern.

With reference back to FIG. 6, at 604, the one or more processors analyze the COI from the CA signals to determine whether the COI from the CA signals exceeds a threshold. For example, the decision at 604 may determine whether the intrinsic PR interval is below a threshold, such as below 250 ms. When the intrinsic PR interval is less than 250 ms, the potential exists that the patient may be experiencing LBBB. Thus, flow moves to 606. Alternatively, when the intrinsic PR interval is equal to or greater than 250 ms, the process interprets the condition as an indication that the patient is not experiencing LBBB, and thus flow moves to 608.

At 606, the one or more processors apply one or more additional criteria to determine whether the patient is experiencing LBBB. In one example, patient data may be obtained from a memory, such as a storage device regarding whether the patient is known to have LBBB. Additionally or alternatively, further patient data may be collected from one or more monitors and analyzed by the one or more processors using an algorithm, lookup table, decision tree, mathematical model, mathematical equation, etc. As another example, the patient data may be obtained through a graphic user interface (GUI), direct ECG or IEGM measurements, patient records, based on S1 heart sounds, based on measurements taken at the time of implant or during a clinical visit, or the like. If at 606, the one or more processors determine that the patient is not experiencing LBBB, flow again moves to 608. Alternatively, if the one or more processors determine that the patient is experiencing LBBB, flow moves to 614.

At 608, the one or more processors select a BiV pacing mode in which simultaneous LV+RV(late) pacing is provided. The BiV pacing mode may be desirable when the patient is not experiencing LBBB. For example, the BiV pacing mode may time pacing pulses to be delivered in the RV and in the LV, where the LV pacing site is identified as the last LV sensing site that experienced intrinsic activation, when the intrinsic PR interval was determined.

At 610, the one or more processors measure and evaluate S1 heart sounds while delivering BiV pacing therapy over a collection of heartbeats, for which the AV delay is adjusted over a predetermined AV delay range with predetermined increments. In one example, the process 300 of FIG. 3 is utilized to adjust the pacing treatment. In another example, the process 500 of FIG. 5 is utilized to adjust the pacing treatment. For example, in connection with each AV delay, S1 heart sounds are measured, and the S1 heart sound duration is identified, prior to incrementing or decrementing the AV delay to the next level. In one example, the AV delay is adjusted over a range between 140-200, with 20 ms increments. In this manner, a first AV delay is provided that is 140 ms, and the S1 heart sound duration is determined, then for a next cycle the AV delay is 160 ms and the S1 heart sound duration is determined, then for the next cycle the AV delay is 180 ms and S1 heart sound duration is determined, and finally the AV delay is 200 ms and the S1 heart sound duration is determined. Each different S1 heart sound duration determined for the corresponding different AV delay then becomes a candidate S1 heart sound provided for selection.

At 612, the one or more processors select the AV delay based on the candidate S1 heart sounds determined. In one example, the AV delay is selected utilizing the process as detailed in relation to FIG. 3, and alternatively utilizing the process as detailed in relation to FIG. 5. In another embodiment, the AV delay is based on the narrowest S1 heart sound duration determined when the different AVDs are utilized to determine the S1 heart sound.

If on the other hand, at 606, the one or more processors determine the patient is experiencing LBBB, flow moves to 614. At 614, the one or more processors select LV only pacing where RV pacing does not occur. By selecting LV only pacing, battery life and energy is saved by not utilizing RV pacing during a pacing treatment.

At 616, the one or more processors evaluate the selected LV only pacing again by monitoring S1 heart sounds. In one example, the process 300 of FIG. 3 is utilized to adjust the pacing treatment. In another example, the process 500 of FIG. 5 is utilized to adjust the pacing treatment. Specifically, the S1 sound signal duration is evaluated for several AVD.

At 618, the one or more processors select the AVD. In one example, the AV delay is selected using the process as detailed in relation to FIG. 3. In another example, the AV delay is selected using the process as detailed in relation to FIG. 5. In another embodiment, the AV delay is selected based on the narrowest S1 sound interval determined.

In all, if the patient has a device measured PR interval less than a threshold, such as 250 ms, and also has LBBB, LV only pacing from the latest activating electrode ($LV_{late}$) is programmed. Offsets can then be utilized, and S1 sound intervals recorded to determine the timing of the pacing treatment. In one example, the offset corresponding to the narrowest S1 signal is used as the offset for pacing therapy. On the other hand, if LBBB is not present and/or PR interval is greater than the threshold, such as 250 ms, biventricular pacing is programmed (e.g. RV+LV simultaneous pacing). During biventricular pacing, S1 sound intervals are also measured at varying programmed AV delay (e.g. 140 up to 200 ms, with 20 ms increments). S1 intervals are recorded and the AV delay resulting in the narrowest S1 signal again is utilized. Similarly, VV delays (e.g. RV first by 20 ms and LV first by 20 ms) can also be adjusted for which an S1 delay is record. The VV delay resulting in a narrower S1 signal can thus similarly be utilized during biventricular pacing.

Figure 8:
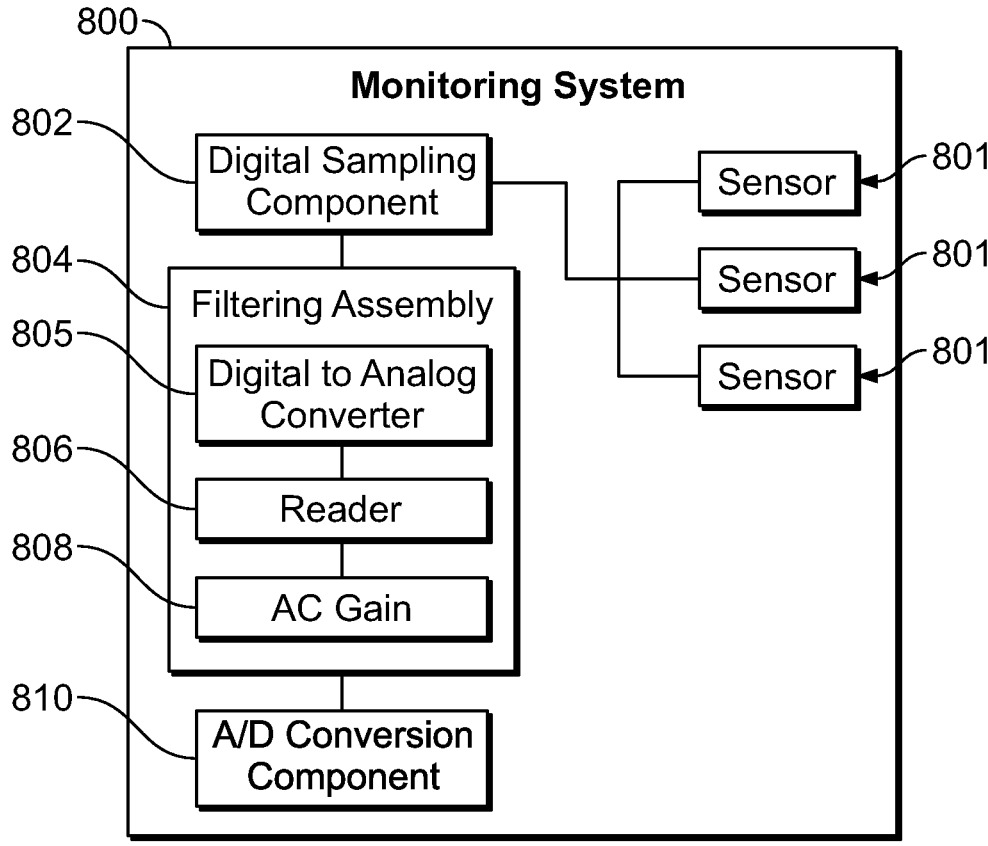
FIG. 8 illustrates a schematic of a monitoring system in accordance with embodiments herein.

FIG. 8 illustrates a schematic diagram of a monitoring system 800 that may be used to detect and determine heart sounds, including S1 sound intervals, and S2 sound intervals. In one example, the monitoring system is or includes an accelerometer. In one embodiment when the monitoring system 800 is a three-dimensional accelerometer, the three-dimensional accelerometer may be a chip for placement in an IMD. In another embodiment, the accelerometer is formed and operates in the manner described in U.S. Pat. No. 6,937,900, titled "AC/DC Multi-Axis Accelerometer For Determining A Patient Activity And Body Position," the complete subject matter which is expressly incorporated herein by reference. In yet another embodiment, the accelerometer is formed and operates in the manner described in U.S. Provisional Patent Application 63/021,775, titled Method and System for Heart Condition Detection Using an Accelerometer, the complete subject matter which is expressly incorporated herein by reference. In an embodiment, when the monitoring system is an accelerometer, the accelerometer includes sensors that generate first (X), second (Y) and third (Z) accelerometer signals along corresponding X, Y and Z axes (also referred to as first axis accelerometer signals, second axis accelerometer signals and third axis accelerometer signals). The X, Y and Z axes accelerometer signals collectively define a three-dimensional, or multi-dimensional (MD) accelerometer data set. While examples herein are described in connection with an accelerometer that generates accelerometer signals along three orthogonal axes, it is recognized that embodiments may be implemented wherein accelerometer signals are generated along two or more axes, including more than three axes.

The monitoring system 800 may include sensors 801 that monitor and receive signals from the X, Y and Z axes. In one embodiment, the individual X, Y and Z signals are received by a digital sampling component 802 that receives a digital input. Coupled to the digital sampling component 802 is a filtering assembly 104 that may include a digital to analog converter 805 to form an alternating current (AC) signal, a reader device 806, and an AC gain device 108. While in this embodiment, the filtering assembly includes the devices provided, in other examples, other devices may be utilized to filter the digital input signal for processing.

The monitoring system 800 may also include an analog to digital conversion component 810, along with a position, or direct current (DC) component. In one example, the analog to digital conversion component may be an 8-bit analog to digital converter (ADC). The evaluation version of the monitoring system 100 may provide 3-axis (X and Y along the chip, Z normal to the chip) DC-coupled posture signal corresponding to 3 orthogonal directions as well as 3-axis AC-coupled activity signal. In one embodiment, each of the 6 signal may be sampled at 100 Hz and accumulated over 1 sec for a total of 12 signals([X/Y/Z],[posture/activity], [100/1 Hz]). This MD accelerometer data may be used to describe embodiments herein.

While described as a digital signal in relation to FIG. 8, in other embodiments the signal may be an analog signal, filtered, amplified, etc. The accelerometer data signals may be recorded in a data storage of the accelerometer, of an IMD, of a remote device etc. Alternatively, the accelerometer data set may be obtained from a remote device, or received from a storage device coupled to the accelerometer. To this end, the accelerometer data set may be a multi-dimensional accelerometer data set.

Figure 9:
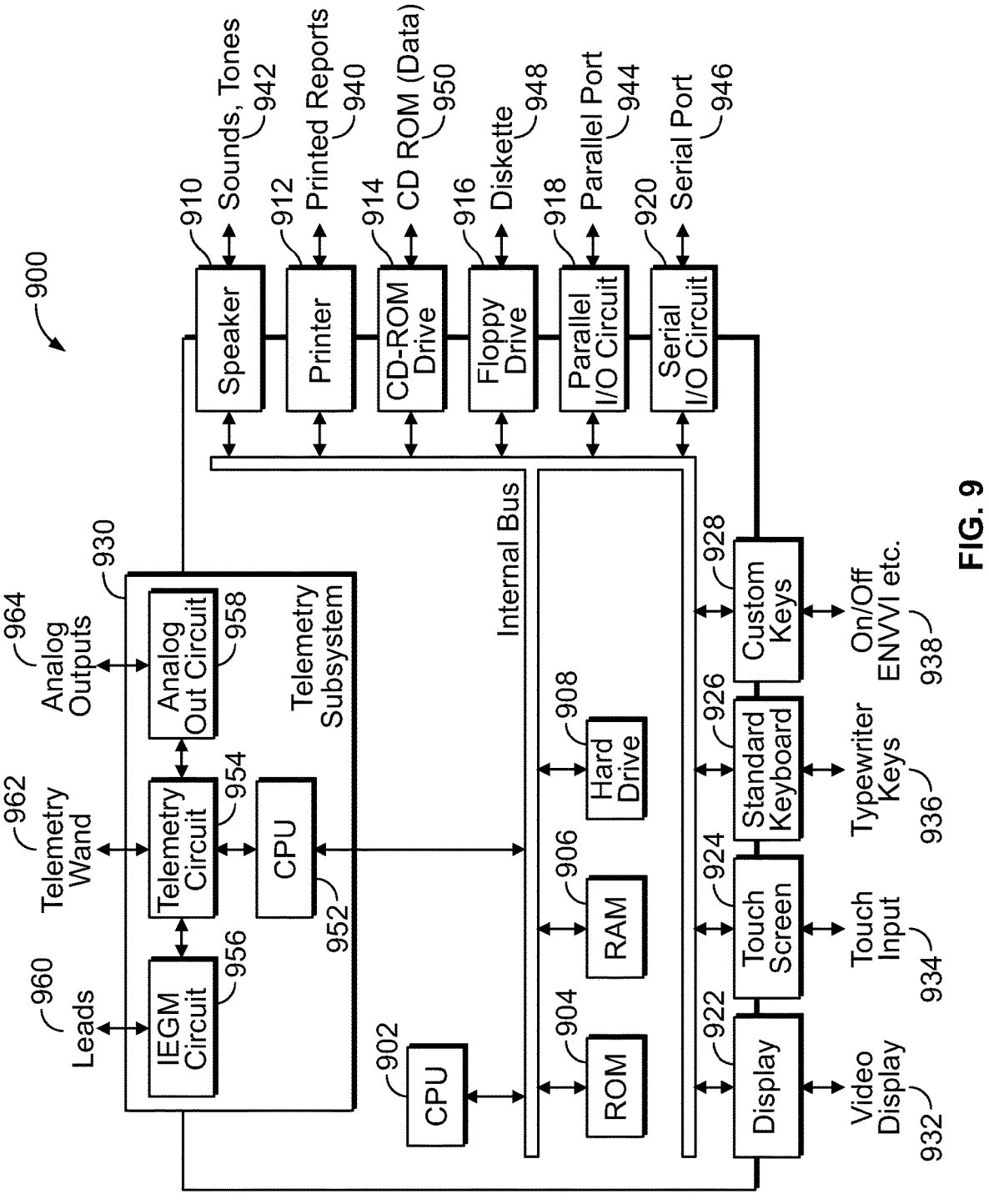
FIG. 9 illustrates a functional block diagram of the external device that is operated in accordance with the processes described herein and to interface with implantable medical devices as described herein.

FIG. 9 illustrates a functional block diagram of the external device 900 that is operated in accordance with the processes described herein and to interface with implantable medical devices as described herein. The external device 900 may be a workstation, a portable computer, an IMD programmer, a PDA, a cell phone, and the like. The external device 900 includes an internal bus that connects/interfaces with a Central Processing Unit (CPU) 902, ROM 904, RAM 906, a hard drive 908, the speaker 910, a printer 912, a CD-ROM drive 914, a floppy drive 916, a parallel I/O circuit 918, a serial I/O circuit 920, the display 922, a touch screen 924, a standard keyboard connection 926, custom keys 928, and a telemetry subsystem 930. The internal bus is an address/data bus that transfers information between the various components described herein. The hard drive 908 may store operational programs as well as data, such as waveform templates and detection thresholds.

The CPU 902 typically includes a microprocessor, a microcontroller, or equivalent control circuitry, designed specifically to control interfacing with the external device 900 and with the IMD 100. The CPU 902 may include RAM or ROM memory, logic and timing circuitry, state machine circuitry, and I/O circuitry to interface with the IMD 100. The CPU 902 may implement some or all of the operations of the control circuitry 233 (FIG. 2). The CPU 902 may implement some or all of the operations of the methods described herein.

The display 922 (e.g., may be connected to the video display 932). The touch screen 924 may display graphic information relating to the IMD 100. The display 922 displays various information related to the processes described herein. The touch screen 924 accepts a user's touch input 934 when selections are made. The keyboard 926 (e.g., a typewriter keyboard 936) allows the user to enter data to the displayed fields, as well as interface with the telemetry subsystem 930. Furthermore, custom keys 928 turn on/off 938 (e.g., EVVI) the external device 900. The printer 912 prints copies of reports 940 for a physician to review or to be placed in a patient file, and speaker 910 provides an audible warning (e.g., sounds and tones 942) to the user. The parallel I/O circuit 918 interfaces with a parallel port 944. The serial I/O circuit 920 interfaces with a serial port 946. The floppy drive 916 accepts diskettes 948. Optionally, the floppy drive 916 may include a USB port or other interface capable of communicating with a USB device such as a memory stick. The CD-ROM drive 914 accepts CD ROMs 950.

The telemetry subsystem 930 includes a central processing unit (CPU) 952 in electrical communication with a telemetry circuit 954, which communicates with both an IEGM circuit 956 and an analog out circuit 958. The circuit 956 may be connected to leads 960. The circuit 956 is also connected to the implantable leads to receive and process IEGM cardiac signals as discussed above. Optionally, the IEGM cardiac signals sensed by the leads may be collected by the IMD 100 and then transmitted to the external device 900, wirelessly to the telemetry subsystem 930 input.

The telemetry circuit 954 is connected to a telemetry wand 962. The analog out circuit 958 includes communication circuits to communicate with analog outputs 964. The external device 900 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 900 to the IMD 100.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system."

Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for controlling an adaptive pacing therapy using an implantable medical device (IMD) having electrodes proximate to an atrial (A) site and at least one ventricular site, the method comprising:

setting a ventricular-ventricular (VV) delay;

measuring an S1 heart sound characteristic of interest (COI) including utilizing the WV delay in connection with delivering the pacing therapy by the IMD;

adjusting the VV delay based on the heart sound COI;

repeating the measuring and adjusting such that a collection of S1 heart sound COIs have corresponding VV delays;

selecting one of the VV delays, that corresponds to a select one of the S1 heart sound COIs, as a resultant VV delay; and managing the pacing therapy, utilized by the IMD, based on the resultant VV delay.

2. The method of claim 1, further comprising:

when repeating the measuring, determining whether a count threshold has been met regarding a number of measurements taken; and selecting the one of the WV delays in response to reaching the count threshold.

3. The method of claim 1, further comprising:

providing an electrode configured to be located proximate to an atrial (A) site; and providing an electrode configured to be located proximate to at least one of the following ventricular sites: left ventricular (LV) site, right ventricular (RV) site of the heart, or HIS site or left bundle branch (LBB) site of the heart.

4. The method of claim 1, wherein the pacing therapy is LV only pacing when the heart exhibits a left bundle branch block (LBBB).

5. The method of claim 1, wherein the pacing therapy is biventricular (BiV) pacing when the heart does not exhibit left bundle branch block (LBBB).

6. The method of claim 1, wherein the measuring the S1 heart sound characteristic of interest (COI) comprises measuring the S1 heart sound COI with a three-dimensional accelerometer.

7. The method of claim 6, wherein the measuring the S1 heart sound COI with the three-dimensional accelerometer includes one of measuring the S1 heart sound COI on a single axis or measuring the S1 heart sound COI based on a composite of at least two axes.

8. The method of claim 1, further comprising:

obtaining a left bundle branch (LBB) block indicator indicative of whether a LBB block is present.

9. The method of claim 1, wherein the VV delay is set by determining a WV offset and subtracting the VV offset from a VV interval.

10. The method of claim 1, further comprising:

adjusting the VV delay by an amount that is proportional to an amount that the S1 heart sound COI is above or below a corresponding threshold.

11. A system for controlling an adaptive pacing therapy using an implantable medical device (IMD) having electrodes proximate to an atrial (A) site at least one ventricular site, comprising:

memory to store specific executable instructions;

one or more processors configured to execute the specific executable instructions for:

setting a ventricular-ventricular (VV) delay;

measuring an S1 heart sound characteristic of interest (COI) including utilizing the WV delay in connection with delivering the pacing therapy by the IMD;

adjusting the VV delay based on the heart sound COI;

repeating the measuring and adjusting such that a collection of S1 heart sound COIs have corresponding VV delays;

selecting one of the VV delays, that corresponds to a select one of the S1 heart sound COIs, as a resultant VV delay; and managing the pacing therapy, utilized by the IMD, based on the resultant VV delay.

12. The system of claim 11, wherein the one or more processors are further configured to:

when repeating the measuring, determining whether a count threshold has been met regarding a number of measurements taken; and selecting the one of the VV delays in response to reaching the count threshold.

13. The system of claim 11, further comprising:

a first electrode configured to be located proximate to an atrial (A) site; and a second electrode configured to be located proximate to at least one of the following ventricular sites: left ventricular (LV) site of the heart, right ventricular (RV) site of the heart, or HIS site or left bundle branch (LBB) site of the heart.

14. The system of claim 11, wherein the pacing therapy is LV only pacing when the heart exhibits a left bundle branch block (LBBB).

15. The system of claim 11, wherein the pacing therapy is biventricular (BiV) pacing when the heart does not exhibit a left bundle branch block (LBBB).

16. The system of claim 11, further comprising a three-dimensional accelerometer coupled to the one or more processors to measure the S1 heart sound characteristic of interest (COI).

17. The system of claim 16, wherein the three-dimensional accelerometer measures one of the S1 heart sound COI on a single axis, or the S1 heart sound COI based on a composite of at least two axes.

18. The system of claim 11, wherein the one or more processors are further configured to execute instructions for obtaining a left bundle branch (LBB) block indicator indicative of whether a LBB block is present.

19. The system of claim 11, wherein the one or more processors are further configured to execute instructions to set the VV delay by determining a VV offset and subtracting the VV offset from a VV interval.

20. The system of claim 11, wherein the one or more processors are further configured to execute instructions to adjust the VV delay by an amount that is proportional to an amount that the S1 heart sound COI is above or below a corresponding threshold.

* * * * *